US009465911B2

(12) United States Patent
Hazebroek et al.

(10) Patent No.: US 9,465,911 B2
(45) Date of Patent: Oct. 11, 2016

(54) PREDICTION OF PHENOTYPES AND TRAITS BASED ON THE METABOLOME

(75) Inventors: Jan Hazebroek, Johnston, IA (US); James Janni, Johnston, IA (US); Jon Lightner, Des Moines, IA (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 746 days.

(21) Appl. No.: 13/297,584

(22) Filed: Nov. 16, 2011

(65) Prior Publication Data

US 2012/0119080 A1    May 17, 2012

Related U.S. Application Data

(60) Provisional application No. 61/414,645, filed on Nov. 17, 2010.

(51) Int. Cl.
    *B01D 15/08*    (2006.01)
    *G01N 33/48*    (2006.01)
    (Continued)

(52) U.S. Cl.
    CPC ............... *G06F 19/24* (2013.01); *A01H 1/04* (2013.01); *A01H 3/00* (2013.01); *B01D 15/08* (2013.01);
    (Continued)

(58) Field of Classification Search
    CPC ....... B01D 15/08; B01D 15/26; G06F 19/10; G06F 19/12; G06F 19/18; G06F 19/24; G01J 3/00; G01J 2003/00; G01J 3/28; G01J 2003/283; G01J 2003/2833; G01J 2003/2836; G01G 7/48; G01G 7/75; G01N 33/48; G01N 33/483; G01N 33/4833; G01N 30/02; G01N 30/04; G01N 30/06; G01N 30/72; G01N 30/7233; G01N 30/86; G01N 30/862; G01N 30/8651; G01N 30/8655; G01N 30/8675; G01N 30/8693; G01N 33/0098
    USPC ............ 210/656; 356/72, 73, 300, 319, 302, 356/326; 436/161, 171; 702/19, 20, 22, 23, 702/24; 703/2, 9, 11
    See application file for complete search history.

(56) References Cited

U.S. PATENT DOCUMENTS 6,229,142 B1    5/2001   Bateman et al.
6,873,914 B2 *  3/2005   Winfield et al. ................ 702/19

(Continued)

FOREIGN PATENT DOCUMENTS

AR    P110104281    11/2011
AU    2011328963    11/2011
(Continued)

OTHER PUBLICATIONS

Fiehn et al., "Metabolic profiling for plant functional genomics", Nature Biotechnology, 2000, vol. 18, pp. 1157-1161.*

(Continued)

*Primary Examiner* — Joseph Drodge

(74) *Attorney, Agent, or Firm* — Pioneer Hi-Bred Intl. Inc.

(57) ABSTRACT

The invention provides methods for characterizing metabolic profiles, phenotypic profiles and trait profiles in plants or groups of plants. Additionally, methods for establishing an unbiased model between a phenotypic profile and a metabolic profile, or between a trait profile and metabolic profile, are also provided by the invention. Further, methods for using such unbiased models to accurately predict the development of a phenotype of interest or a trait of interest in an independent, immature plant are also provided. In one embodiment, immature plants are selected for use based on their predicted development of a phenotype or trait of interest.

59 Claims, 6 Drawing Sheets

Figure 1:
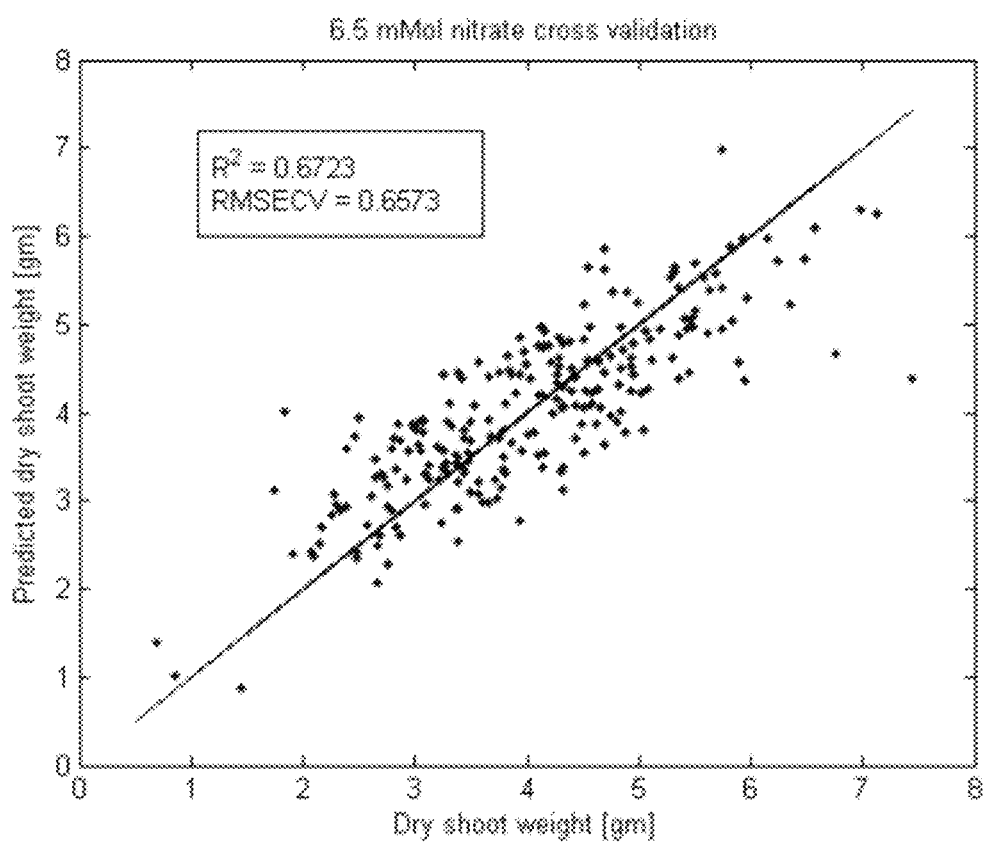

(51) Int. Cl.
G01N 30/02 (2006.01)
G01N 30/86 (2006.01)
G06F 19/12 (2011.01)
A01C 1/00 (2006.01)
A01H 1/04 (2006.01)
A01H 3/00 (2006.01)
G06F 19/24 (2011.01)
G01N 33/483 (2006.01)
G06F 19/18 (2011.01)

(52) U.S. Cl.
CPC ...... *G01N 30/8675* (2013.01); *G01N 33/4833* (2013.01); *G06F 19/12* (2013.01); *G06F 19/18* (2013.01)

(56) References Cited

U.S. PATENT DOCUMENTS

| | | | |
|---|---|---|---|
| 7,384,387 B1* | 6/2008 | Raillard et al. | 506/12 |
| 2003/0023386 A1* | 1/2003 | Aranibar et al. | 702/19 |
| 2003/0060690 A1* | 3/2003 | Jelliffe et al. | 600/300 |
| 2003/0229451 A1* | 12/2003 | Hamilton et al. | 702/19 |
| 2004/0172678 A1* | 9/2004 | Gressel et al. | 800/278 |
| 2006/0080040 A1* | 4/2006 | Garczarek | G01N 30/8624 702/19 |
| 2008/0127367 A1* | 5/2008 | Davies et al. | 800/278 |
| 2008/0133143 A1* | 6/2008 | Gustafsson et al. | 702/19 |
| 2008/0233576 A1* | 9/2008 | Weston et al. | 435/6 |
| 2008/0234945 A1* | 9/2008 | Walk et al. | 702/19 |
| 2008/0234948 A1* | 9/2008 | Walk et al. | 702/23 |
| 2009/0024360 A1* | 1/2009 | Arnvidarson | 702/189 |
| 2010/0145625 A1 | 6/2010 | Altmann et al. | |
| 2011/0125477 A1* | 5/2011 | Lightner et al. | 703/11 |
| 2011/0294700 A1* | 12/2011 | Thelen et al. | 506/12 |

FOREIGN PATENT DOCUMENTS

| | | |
|---|---|---|
| BR | 1120130120681 | 11/2011 |
| CA | 2817241 | 11/2011 |
| CL | 1399-2013 | 11/2011 |
| EP | 11791143.8 | 11/2011 |
| WO | WO 03/046798 A1 | 6/2003 |
| WO | WO 2007/118215 A2 | 10/2007 |
| WO | WO 2008/077635 A1 | 7/2008 |
| WO | PCT/US2011/060936 | 11/2011 |
| WO | WO-2012/068217 | 5/2012 |

OTHER PUBLICATIONS

Fiehn, "Combining genomics, metabolome analysis, and biochemical modelling to understand metabolic networks", Comp Funct Genom, 2001, vol. 2, pp. 155-168.*
Joerg et al, "PAG-XIV (P890) Image-Based High Throughput Phenotyping of Complete Plants", Plant & Animal Genomes XIV Conference, presented at Town & Country Convention Center, Jan. 14-18, 2006.*
Christophe et al, "Traitmill: a functional genomoics platform for the phenotypic analysis of cereals", Plant Genetics Resources vol. 4(1): pp. 20-24, Sep. 13, 2005.*
Douglas C. Boyes, "Growth Stage-Based Phenotypic Analysis of Arabidopsis: A Model for High Throughput Functional Genomics in Plants", The Plant Cell, vol. 13, pp. 1499-1510, Jul. 2001.*
El-Lithy, M., et al., "Quantitative Trait Locus Analysis of Growth-Related Traits in a New Arabidopsis Recombinant Inbred Population," *Plant Physilogy*, 2004,vol. 135, pp. 444-458.
Fiehn, Oliver, Metabolomics—the link between genotypes and phenotypes, *Plant Molecular Biology*, 2002, vol. 48, pp. 155-171.
Keurentjes, J., et al., "The genetics of plant metabolism," *Nature Genetics*, 2006, vol. 38(7), pp. 842-849.
Meyer, R., et al., "The metabolic signature related to high plant growth rate in *Arabidopsis thaliana,*" *PNAS*, 2007, vol. 104(11), pp. 4759-4764.
Roessner, U., et al., "Metabolic Profiling Allows Comprehensive Phenotyping of Genetically or Environmentally Modified Plant Systems," *The Plant Cell*, 2001, vol. 13, pp. 11-29.
"Vip—Eigenvector Documentation Wiki," retrieved from http://wiki.eigenvector.com/index.php?title=Vip&oldid=8120 (Jun. 9, 2014).
Mehmood, T., et al. "A review of variable selection methods in partial least squares regression," Chemometrics and Intelligent Laboratory Systems, vol. 118, pp. 62-69 (2012).

* cited by examiner

PREDICTION OF PHENOTYPES AND TRAITS BASED ON THE METABOLOME

CROSS-REFERENCE TO RELATED APPLICATIONS

This application claims the benefit of U.S. Provisional Application 61/414,645, filed Nov. 17, 2010, herein incorporated by reference in its entirety.

FIELD OF THE INVENTION

The invention relates to the field of metabolomics and, more particularly, the use of metabolomics data and statistical analyses to predict phenotypes and traits in plants.

BACKGROUND OF THE INVENTION

The agricultural industry continuously develops new plant varieties which are designed to produce high yields under a variety of environmental and adverse conditions. At the same time, the industry also seeks to decrease the costs and potential risks associated with traditional approaches such as fertilizers, herbicides and pesticides. In order to meet these demands, plant breeding techniques have been developed and used to produce plants with desirable phenotypes. Such phenotypes may include, for example, increased crop quality and yield, increased crop tolerance to environmental conditions (e.g., drought, extreme temperatures), increased crop tolerance to viruses, fungi, bacteria, and pests, increased crop tolerance to herbicides, and altering the composition of the resulting crop (e.g., increased sugar, starch, protein, or oil).

To breed plants which exhibit a desirable phenotype, a wide variety of ancient (e.g., cross-breeding, hybridization) and modern (e.g., recombinant DNA technology) techniques can be employed. A crucial step in any of these methodologies is the assessment of phenotypes and traits in the altered plants. Although strategies have been developed to reduce the time and expense required for making such assessments, significant time and cost are still necessary to evaluate crops under different stresses, seasons and environmental conditions. As a result, much effort has been made to increase throughput, lower cost and increase the accuracy and precision of evaluating new plant varieties.

One approach to assess new plant varieties is to screen their genomes to determine if they contain genes of interest. This can be accomplished using indirect (e.g., marker assisted selection) or direct detection methods (e.g., southern blots) that determine whether or not a gene of interest is expressed in a plant without having to grow the plant to maturity. However, a drawback of this approach is that it requires knowledge of the particular gene of interest and does not necessarily produce a reliable prediction of the phenotype of the plant at maturity. Other techniques, such as RNA or protein screening, suffer from similar drawbacks, in that genes of interest must be known and that the accuracy and precision of predicting the plant's phenotype are relatively low. As a result, the development of techniques that could accurately predict the development of phenotypes or traits in altered plants, and eliminate the need for growing such plants to maturity under many simulated conditions, would be particularly advantageous.

Metabolomics is the systemic study of the complete set of metabolites (i.e., the metabolome) found in a biological cell, tissue, organ or organism at a given point in time. In plants, metabolomics allows for an unbiased measurement of the metabolite biochemistry that evolves as light energy, water, carbon dioxide and nutrients are converted into biomass within a changing environment. Time scales of this biochemistry range from seconds to months, and variability within the metabolome of an organism may be regulated by alterations in gene expression, stresses or changes in the environment. Although efforts have been made to relate the metabolome of a new plant variety to a phenotype or trait of interest, such studies can be challenging and imprecise.

Traditional metabolome analysis is complex, expensive and time consuming. Typically, the metabolic profiles of altered and unaltered plants (or plant tissues or organs) must be produced. Such plants may need to be grown to maturity under a variety of environmental conditions or under different types of stress. Metabolic profiles usually consist of named metabolites whose identities may or may not be known. High fidelity naming and quantification of metabolites is typically slow and labor intensive. Subsequently, comparisons must be made between the metabolomes of the altered and unaltered plants to determine differences in specific metabolite levels. Amounts of known metabolites among this subgroup are often mapped onto specific metabolic pathways. Finally, predictions can be made to determine what effect, if any, the observed differences may have had on the phenotype or trait of interest. Thus, the use of metabolomics for evaluating and predicting plant phenotypes can be complex and costly.

As such, the development of simple and inexpensive methods that are capable of accurately relating the metabolome to phenotypes or traits in new plant varieties would be extremely beneficial to the agricultural industry. Additionally, methods which could accurately predict the development of such phenotypes or traits early in a plant's life cycle would be particularly advantageous. Furthermore, the development of chemometric models that would eliminate the need to grow new plant varieties under various environmental conditions or under different types of stress in order to predict the development of a phenotype or trait of interest would also be particularly valuable.

BRIEF SUMMARY OF THE INVENTION

Methods for characterizing metabolic profiles, phenotypic profiles and trait profiles in plants are provided. Additionally, methods for establishing an unbiased model between a phenotypic profile and a metabolic profile, or between a trait profile and metabolic profile, are also provided by the invention. Such unbiased models are useful in accurately predicting the development of a phenotype of interest or a trait of interest in an independent, immature plant. For example, in one embodiment of the invention, an unbiased model is established that identifies correlations between the metabolic profile and the phenotypic or trait profile of two or more groups of plants. Subsequently, the identified correlations can be used to predict the development of a phenotype or trait in an independent plant where only the metabolic profile has been characterized.

In one embodiment of the invention, an unbiased model is established using the phenotypic profiles and metabolic profiles of at least two groups of plants, wherein the groups of plants exhibit different phenotypes or are grown under different environmental conditions. Alternatively, an unbiased model can be established using the trait profiles and metabolic profiles of at least two groups of plants, wherein the groups of plants exhibit different traits or are grown under different environmental conditions. In such embodiments, the unbiased models of the invention may be determined using various combinations of partial least squares analysis, partial least squares discriminant analysis, principal component analysis, cross-validation, variable importance for projection calculations, support vector machines and neural networks.

The metabolic profiles of the plants or groups of plants encompassed by the invention may be characterized, for example, using chromatography and mass spectrometry techniques. In a particular embodiment, the mass-to-charge fragments detected by mass spectrometry, which comprise the raw metabolic profiles of the invention, are not identified, characterized or otherwise biased prior to statistical analysis. Only signal denoising, alignment, baseline correction, and normalization pre-processing steps are performed. Thus, the metabolic profiles of the invention comprise the entire set of metabolites which are detected and pre-processed.

Methods are also provided for predicting the development of a phenotype or trait of interest in an independent plant that was not used to establish the unbiased model of the invention. In one embodiment, the unbiased models of the invention are applied to the metabolic profile of an immature, independent plant in order to predict the development of a phenotype or trait of interest in the plant. In another such embodiment, immature plants are selected based on their predicted develop of a phenotype or trait of interest.

The following embodiments are encompassed by the present invention:

1. A method for establishing an unbiased model using the metabolic profile and phenotypic profile of at least two groups of plants, said method comprising:
   a) characterizing the phenotypic profiles of said at least two groups of plants, wherein said at least two groups of plants have different phenotypes, or wherein said at least two groups of plants are grown under different environmental conditions;
   b) extracting metabolites from said at least two groups of plants;
   c) separating said metabolites by chromatography to generate a first set of data;
   d) detecting the mass-to-charge fragments produced by said metabolites using mass spectrometry to generate a second set of data;
   e) pre-processing said first set of data and said second set of data to align, reduce noise and dimensionality, and normalize;
   f) using the pre-processed data of step (e) to build a partial least squares multivariate calibration to predict quantitative outcomes;
   g) using validation or cross-validation to select latent variables; and,
   h) providing an output to a user of said unbiased model.

2. The method of embodiment 1, further comprising predicting a phenotype in a plant, said predicting comprising:
   a) determining the metabolic profile of at least one independent plant, wherein said at least one independent plant is not mature; and,
   b) using said unbiased model of embodiment 1 and said metabolic profile of said at least one independent plant to predict expression of said phenotype in said at least one independent plant.

3. A method for selecting a plant that is predisposed to express a phenotype of interest, said method comprising:
   a) using the method of embodiment 2 to predict expression of said phenotype of interest in said at least one independent plant; and,
   b) selecting said at least one independent plant which is predicted to express said phenotype of interest.

4. The method of embodiment 3, wherein said at least one independent plant comprises at least one transgene.

5. The method of any one of the preceding embodiments, wherein said method of building partial least squares multivariate calibrations further comprises the use of partial least squares discriminant analysis.

6. The method of any one of the preceding embodiments, wherein outliers in said unbiased model are identified using principal component analysis and cross-validation.

7. The method of any one of embodiments 1-4, wherein said unbiased model is established using support vector machines.

8. The method of any one of embodiments 1-4, wherein said unbiased model is established using neural networks.

9. The method of any one of the preceding embodiments, wherein variable importance for projection calculations are used to estimate importance of said metabolites in said unbiased model.

10. The method of any one of the preceding embodiments, wherein separation of said metabolites by chromatography is performed using gas chromatography.

11. The method of any one of the preceding embodiments, wherein said metabolites are detected by mass spectrometry using a time-of-flight mass spectrometer.

12. The method of embodiment 11, wherein said pre-processing of said first set of data and said second set of data to reduce the noise and dimensionality comprises:
   a) fitting the mass-to-charge fragments to a common time grid;
   b) reducing noise and dimensionality using statistical analyses, wherein said statistical analyses includes smoothing, noise subtraction or thresholding;
   c) aligning mass-to-charge fragment retention times or retention indices using a local displacement function;
   d) filtering mass-to-charge fragment×retention times or index combinations using thresholding and consistency functions; and,
   e) normalizing said mass-to-charge fragment×retention times or index intensities for internal standard mass-to-charge intensity and sample dry weight.

13. The method of embodiment 12, further comprising the steps of:
   a) establishing specific retention time or retention index windows;
   b) determining a correlation between said mass-to-charge fragments identified within said specific retention time or retention index windows;
   c) calculating a Pearson correlation coefficient matrix for said mass-to-charge fragments;
   d) clustering said mass-to-charge fragments using a K nearest neighbor agglomerative method, wherein clusters are made when a calculated neighboring distance is less than 1, and wherein said clusters require more than 5 mass-to-charge fragments;
   e) eliminating mass-to-charge fragments that are not within said calculated neighboring distance of said clusters; and,
   f) selecting said mass-to-charge fragments that exhibit a highest frequency of being a maximum within each one of said clusters to represent each said cluster in said unbiased model.

14. The method of any one of the preceding embodiments, wherein said at least two groups of plants are grown under precision growth conditions.

15. The method of any one of the preceding embodiments, wherein said at least one independent plant is grown under precision growth conditions or under natural conditions.

16. The method of any one of the preceding embodiments, wherein said at least two groups of plants possess the same genetic background.

17. The method of any one of the preceding embodiments, wherein said at least one independent plant possesses the same genetic background as said at least two groups of plants.

18. The method of any one of embodiments 1-16, wherein said at least one independent plant possesses a different genetic background from said at least two groups of plants.

19. The method of any one of the preceding embodiments, wherein said at least one independent plant is grown under the same environmental conditions as said at least two groups of plants.

20. The method of any one of embodiments 1-18, wherein said at least one independent plant is grown under different environmental conditions as said at least two groups of plants.

21. The method of any one of the preceding embodiments, wherein said at least one independent plant is grown at the same time as said at least two groups of plants.

22. The method of any one of embodiments 1-20, wherein said at least one independent plant is grown at a different time than said at least two groups of plants.

23. The method of any one of the preceding embodiments, wherein said at least one independent plant is grown at the same location as said at least two groups of plants.

24. The method of any one of embodiments 1-22, wherein said at least one independent plant is grown at a different location than said at least two groups of plants.

25. The method of any one of the preceding embodiments, wherein said different phenotypes of said at least two groups of plants are selected from the group consisting of plant growth, total plant area, biomass, dry shoot weight, yield, yield drag, nitrogen utilization efficiency, water use efficiency, pest resistance, disease resistance, transgene effects, response to chemical treatment, stress tolerance, gas exchange parameters, days to silk, days to shed, germination rate, relative maturity, lodging, ear height, flowering time, stress emergence rate, leaf senescence rate, canopy photosynthesis rate, silk emergence rate, anthesis to silking interval and percent recurrent parent.

26. The method of any one of the preceding embodiments, wherein said different environmental conditions under which said at least two groups of plants are grown are selected from the group consisting of temperature, soil moisture, nitrogen level, insect pressure, disease pressure, soil type, pesticide treatment, herbicide treatment, day length, planting density, light intensity, light quality, tillage practice, day of planting, carbon dioxide levels and oxygen levels.

27. The method of any one of the preceding embodiments wherein said at least two groups of plants, or said at least one independent plant, are monocots or dicots.

28. The method of embodiment 27, wherein said monocots or dicots are maize, rice, barley, oats, millet, wheat, grasses, soybean, cotton, sunflower, safflower, *Arabidopsis*, tobacco, rapeseed, sugarcane, alfalfa, canola, clover, tomato, potato, cassava or sorghum.

29. A method for establishing an unbiased model using the metabolic profile and trait profile of at least two groups of plants, said method comprising:
   a) characterizing the trait profiles of said at least two groups of plants, wherein said at least two groups of plants have different traits, or wherein said at least two groups of plants are grown under different environmental conditions;
   b) extracting metabolites from said at least two groups of plants;
   c) separating said metabolites by chromatography to generate a first set of data;
   d) detecting the mass-to-charge fragments produced by said metabolites using mass spectrometry to generate a second set of data;
   e) pre-processing said first set of data and said second set of data to align, reduce noise and dimensionality and normalize;
   f) using the pre-processed data of step (e) to build a partial least squares multivariate calibration to predict quantitative outcomes;
   g) using validation or cross-validation to select latent variables; and,
   h) providing an output to a user of said unbiased model.

30. The method of embodiment 29, further comprising predicting a trait in a plant, wherein said predicting comprises:
   a) determining the metabolic profile of at least one independent plant, wherein said at least one independent plant is not mature; and,
   b) using said unbiased model of embodiment 29 and said metabolic profile of said at least one independent plant to predict expression of said trait in said at least one independent plant.

31. A method for selecting a plant that is predisposed to express a trait of interest, said method comprising:
   a) using the method of embodiment 30 to predict expression of said trait of interest in said at least one independent plant; and,
   b) selecting said at least one independent plant which is predicted to express said trait of interest.

32. The method of embodiment 31 wherein said at least one independent plant comprises at least one transgene.

33. The method of any one of embodiments 29-32, wherein said method of building partial least squares multivariate calibrations further comprises the use of partial least squares discriminant analysis.

34. The method of any one of embodiments 29-33, wherein outliers in said unbiased model are identified using principal component analysis and cross-validation.

35. The method of any one of embodiments 29-32, wherein said unbiased model is established using support vector machines.

36. The method of any one of embodiments 29-32, wherein said unbiased model is established using neural networks.

37. The method of any one of embodiments 29-36, wherein variable importance for projection calculations are used to estimate importance of said metabolites in said unbiased model.

38. The method of any one of embodiments 29-37, wherein separation of said metabolites by chromatography is performed using gas chromatography.

39. The method of any one of embodiments 29-38, wherein said metabolites are detected by mass spectrometry using a time-of-flight mass spectrometer.

40. The method of embodiment 39, wherein said pre-processing of said first set of data and said second set of data to reduce the noise and dimensionality comprises:
   a) fitting the mass-to-charge fragments to a common time grid;

b) reducing noise and dimensionality using statistical analyses, wherein said statistical analyses includes smoothing, noise subtraction or thresholding;

c) aligning retention times or retention indices using a correlation-based alignment function;

d) filtering mass-to-charge fragment×retention times or index combinations using thresholding and consistency functions; and e) normalizing said mass-to-charge fragment×retention times or index intensities for internal standard mass-to-charge intensity and sample dry weight.

41. The method of embodiment 40, further comprising the steps of:

a) establishing specific retention time or retention index windows;

b) determining a correlation between said mass-to-charge fragments identified within said specific retention time windows;

c) calculating a Pearson correlation coefficient matrix for said mass-to-charge fragments;

d) clustering said mass-to-charge fragments using a K nearest neighbor agglomerative method, wherein clusters are made when a calculated neighboring distance is less than 1, and wherein said clusters require more than 5 mass-to-charge fragments;

e) eliminating mass-to-charge fragments that are not within said calculated neighboring distance of said clusters; and, f) selecting said mass-to-charge fragments that exhibit a highest frequency of being a maximum within each one of said clusters to represent each said cluster in said unbiased model.

42. The method of any one of embodiments 29-41, wherein said at least two groups of plants are grown under precision growth conditions.

43. The method of any one of embodiments 29-42, wherein said at least one independent plant is grown under precision growth conditions or under natural conditions.

44. The method of any one of embodiments 29-43, wherein said at least two groups of plants possess the same genetic background.

45. The method of any one of embodiments 29-44, wherein said at least one independent plant possesses the same genetic background as said at least two groups of plants.

46. The method of any one of embodiments 29-44, wherein said at least one independent plant possesses a different genetic background from said at least two groups of plants.

47. The method of any one of embodiments 29-46, wherein said at least one independent plant is grown under the same environmental conditions as said at least two groups of plants.

48. The method of any one of embodiments 29-46, wherein said at least one independent plant is grown under different environmental conditions as said at least two groups of plants.

49. The method of any one of embodiments 29-48, wherein said at least one independent plant is grown at the same time as said at least two groups of plants.

50. The method of any one of embodiments 29-48, wherein said at least one independent plant is grown at a different time than said at least two groups of plants.

51. The method of any one of embodiments 29-50, wherein said at least one independent plant is grown at the same location as said at least two groups of plants.

52. The method of any one of embodiments 29-50, wherein said at least one independent plant is grown at a different location than said at least two groups of plants.

53. The method of any one of embodiments 29-52, wherein said different traits of said at least two groups of plants are selected from the group consisting of leaf angle, canopy width, leaf width ear fill, scattergrain, root mass, stalk strength, seed moisture, greensnap, shattering, visual pigment accumulation, kernels per ear, ears per plant, kernel size, kernel density, leaf nitrogen content and grain nitrogen content.

54. The method of any one of embodiments 29-53, wherein said different environmental conditions under which said at least two groups of plants are grown are selected from the group consisting of temperature, soil moisture, nitrogen level, insect pressure, disease pressure, soil type, pesticide treatment, herbicide treatment, day length, planting density, light intensity, light quality, tillage practice, day of planting, carbon dioxide levels and oxygen levels.

55. The method of any one of embodiments 29-54, wherein said at least two groups of plants, or said at least one independent plant, are monocots or dicots.

56. The method of embodiment 55, wherein said monocots or dicots are maize, rice, barley, oats, millet, wheat, grasses, soybean, cotton, sunflower, safflower, *Arabidopsis*, tobacco, rapeseed, sugarcane, alfalfa, canola, clover, tomato, potato, cassava or sorghum.

BRIEF DESCRIPTION OF THE SEVERAL VIEWS OF THE DRAWING(S)

FIG. 1 sets forth actual dry shoot weight versus predicted dry shoot weight of inbred corn lines grown under normal nitrogen conditions.

Figure 2:
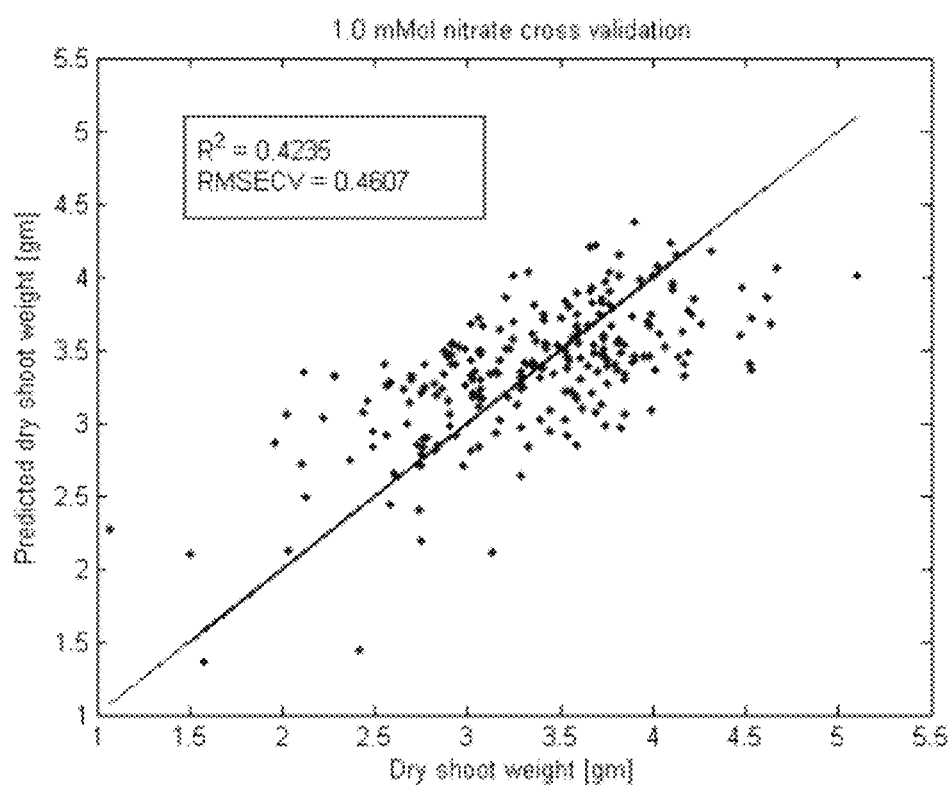

FIG. 2 sets forth actual dry shoot weight versus predicted dry shoot weight of inbred corn lines grown under low nitrogen conditions.

Figure 3:
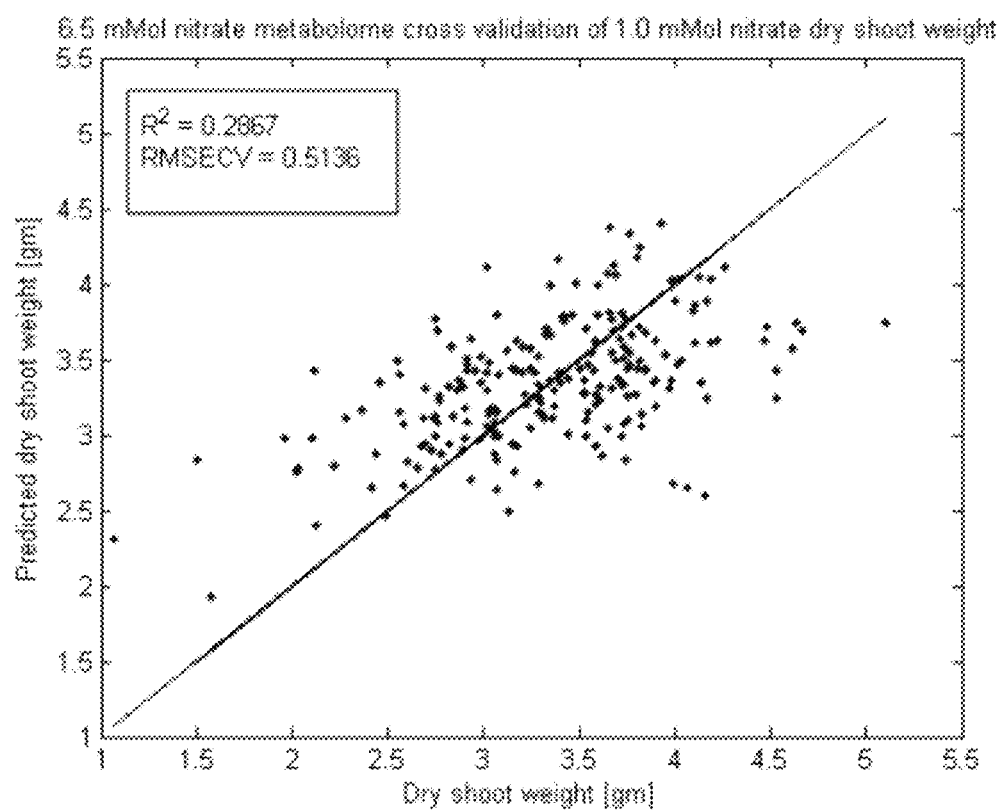

FIG. 3 sets forth actual dry shoot weight of low nitrogen inbred corn lines versus predicted dry shoot weight of the inbred lines, predicted by partial least squares analysis and cross-validation using the metabolome of the inbred lines receiving normal nitrogen.

Figure 4:
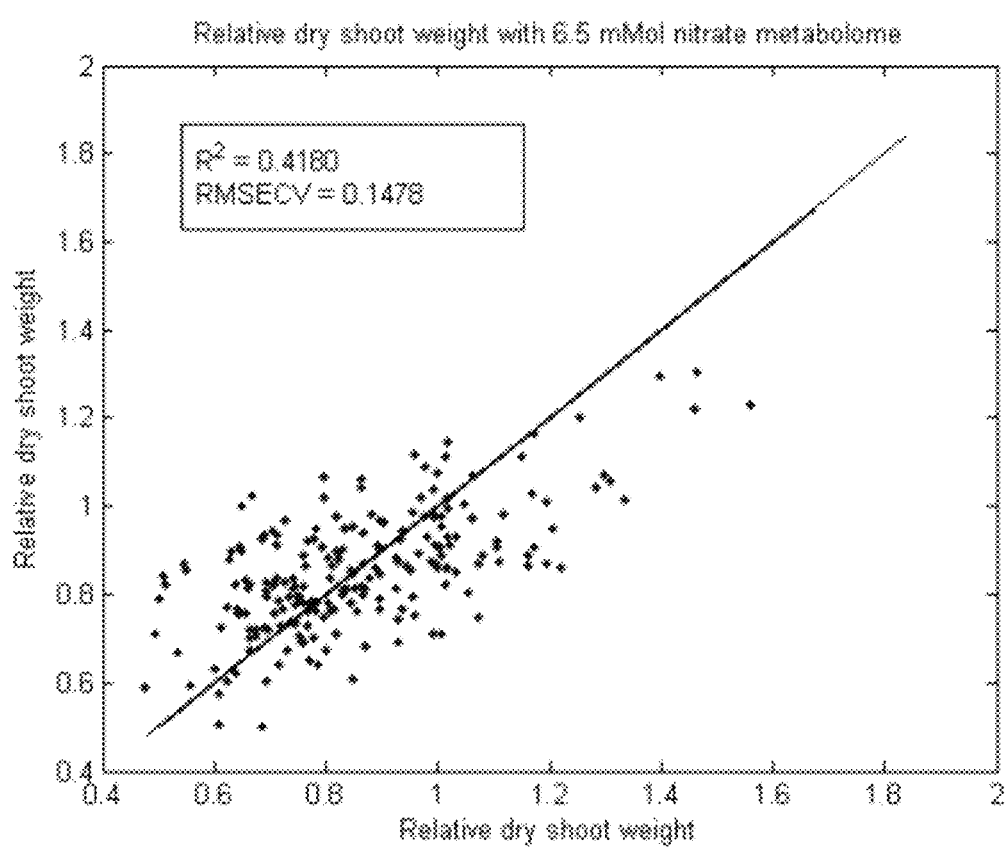

FIG. 4 sets forth the metabolomics based PLS model predicted genotype specific relative dry shoot weight between plants deprived of nitrogen and those receiving sufficient nitrogen plotted against the measured relative dry shoot weight.

Figure 5:
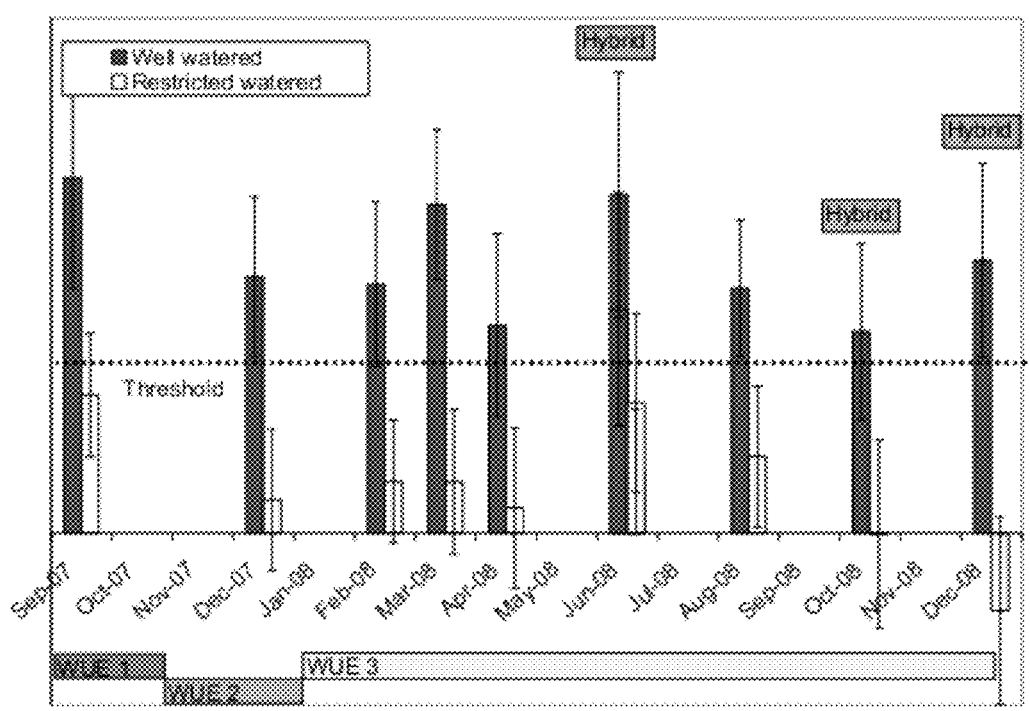

FIG. 5 sets forth modeling of the metabolic changes produced by drought stress across a range of genotypes and environments.

Figure 6:
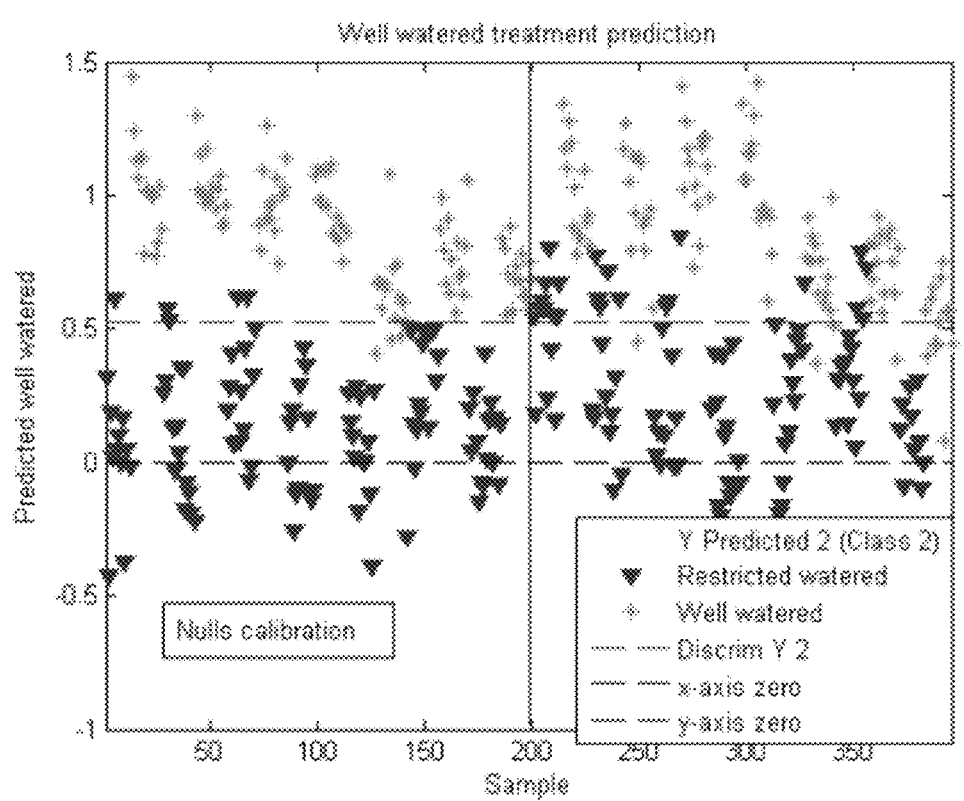

FIG. 6 sets forth the predicted class of transgene events which were statistically separated from the null segregants in the direction predicted using the well-watered metabolome.

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

The invention provides methods for characterizing metabolic profiles, phenotypic profiles and trait profiles in plants or groups of plants. Additionally, methods for establishing an unbiased model between a phenotypic profile and a metabolic profile, or between a trait profile and metabolic profile, are also provided by the invention. Further, methods for using such unbiased models to accurately predict the development of a phenotype of interest or a trait of interest in an independent, immature plant are also provided.

In one embodiment of the invention, an unbiased model is established using the phenotypic profiles and metabolic profiles of at least two groups of plants, wherein the groups of plants exhibit different phenotypes or are grown under different environmental conditions. Alternatively, an unbiased model can be established using the trait profiles and metabolic profiles of at least two groups of plants, wherein the groups of plants exhibit different traits or are grown under different environmental conditions. In such embodiments, the unbiased models of the invention may be determined using various combinations of partial least squares analysis, partial least squares discriminant analysis, principal component analysis, cross-validation, variable importance for projection calculations, support vector machines and neural networks. The metabolic profiles of the plants or groups of plants encompassed by the invention may be characterized, for example, using chromatography and mass spectroscopy techniques. In a particular embodiment, the mass-to-charge fragments detected by mass spectrometry, which comprise the metabolic profiles of the invention, are not identified, characterized or otherwise biased prior to statistical analysis. Only signal denoising, alignment, baseline correction, and normalization pre-processing steps are performed. Thus, the metabolic profiles of the invention comprise the entire set of metabolites which are detected and pre-processed.

Methods are also provided for predicting the development of a phenotype or trait of interest in a plant that was not used to establish the unbiased model of the invention, i.e., in an independent plant. While the independent plant can be a plant at any stage of development, in one embodiment, the unbiased models of the invention are applied to the metabolic profile of an immature, independent plant in order to predict the development of a phenotype or trait of interest in the plant. In another such embodiment, immature plants are selected for use based on their predicted develop of a phenotype or trait of interest.

II. Analytical Techniques for Characterizing the Metabolic Profiles, Phenotypic Profiles and Trait Profiles in a Plant or Groups of Plants Methods of the invention provide means for characterizing metabolic profiles, phenotypic profiles and trait profiles in a plant or group of plants. Embodiments of the invention encompass the use of such profiles to establish unbiased models to predict a phenotype or trait of interest in an independent, immature plant.

As used herein, the terms "metabolic profile" and "metabolome" are intended to mean the collection of metabolites detected in a sample taken from a plant. The term "metabolite" is intended to mean a compound that is produced within an organism due to any process of anabolism or catabolism. The compound is naturally occurring or may be induced by transgene expression. The term "phenotypic profile" is intended to mean the measurable characteristics of a plant that relate to a particular plant function. Similarly, the term "trait profile" is intended to mean the measurable characteristics of a plant that contribute to a particular phenotype of interest. Examples of such traits of interest and phenotypes of interest are described further herein below.

The term "characterizing" is intended to mean the use of analytical methods to collectively describe the components which comprise a profile. In the case of a metabolic profile, "characterizing" means the complete description of the metabolites in a sample taken from a plant. In the case of a phenotypic profile, "characterizing" means the complete description of the measurable characteristics of the plant that relate to a particular plant function. In the case of a trait profile, "characterizing" means the complete description of the measurable characteristics of a plant that contribute to a particular phenotype of interest.

In one embodiment of the invention, the metabolic profile of a plant is characterized by extracting the metabolites from a sample obtained from a plant, or cell, or plant part and detecting such metabolites by various analytical methods. As used herein, the terms "extract" or "extracted" are intended to mean any methods which allow for the isolation of analytes of interest (i.e., metabolites) from a sample matrix or a sample derived therefrom. The term "extraction", or derivations thereof, does not necessarily refer to the removal of all materials or constituents, other than the analytes of interest, from a sample matrix or a sample derived therefrom. Instead, in some embodiments, the term "extraction" refers to a procedure that enriches the amount of one or more analytes of interest relative to one or more other components present in the sample matrix or in a sample derived therefrom. In other embodiments, an "extraction" procedure can be used to remove one or more components of a sample that could interfere with the detection of the analyte. For example, such components could be those that interfere with detection of an analyte ion by mass spectrometry. In yet other embodiments, the extraction procedure is used to remove the analytes of interest from the test sample matrix. Various extraction techniques can be employed to extract or purify analytes of interest from a sample, and the selection of extraction techniques appropriate for extracting analytes of interest from specific plants, or cells, or plant parts, would be known to one of ordinary skill in the art. In a particular embodiment of the invention, the analytes of interest are extracted from a sample using the techniques described in the Examples provided herein below.

The invention further provides methods for separating analytes of interest in an extracted sample, wherein such separation of the analytes of interest facilitates their detection. In one embodiment, separation of the analytes of interest comprises chromatographic separation. As used herein, "chromatographic separation" employs an "analytical column" or a "chromatography column" having sufficient chromatographic plates to effect a separation of the components of a test sample matrix. Preferably, the components eluted from the analytical column are separated in such a way to allow the presence or amount of an analyte(s)

of interest to be determined. "Analytical columns" can be distinguished from "extraction columns," which typically are used to purify or extract retained materials from non-retained materials to obtain a "purified" sample for further purification or analysis.

In particular embodiments of the invention, analytes of interest are chromatographically separated from one another to facilitate their detection. In such embodiments, chromatographic separation of the analytes of interest includes: (a) disposing the composition comprising the extracted analyte(s) onto an analytical column; and (b) eluting the analyte(s) from the analytical column. Suitable chromatography methods include, but are not limited to, high performance liquid chromatography (HPLC), gas chromatography (GC), reverse phase-HPLC, ion-exchange HPLC, gel-permeation chromatography, capillary electrophoresis, electrophoresis, thin-layer chromatography, chip-base micro-fluidic separation, affinity-interaction chromatography using antibodies or other ligand-specific binding domains. It is recognized that, depending on the method of detection employed, it may not be necessary to separate each of the analytes from one another by chromatography. Such methods of detection allow each of the analytes to be detected when present as a mixture.

In one embodiment of the invention, chromatographic separation of the analytes of interest in a sample comprises the use of a gas chromatograph and a GC column. Gas chromatographs typically comprise a GC column and column inlet, which is used to introduce a sample onto the GC column. Various GC columns may be used in the methods of the invention including, but not limited to, packed columns, capillary columns, internally heated microFAST columns and micropacked columns. Any GC column that can sufficiently resolve the analytes of interest and allow for their detection and/or quantification can be employed, and such columns would be known to those of ordinary skill in the art. In a particular embodiment of the invention, the analytes of interest are prepared for separation on a GC column as described in the Examples provided herein below. Data generated by the separation methods described herein are regarded as the "first data set".

The invention further provides methods for detecting the presence of the analytes of interest in an extracted sample. In one embodiment of the invention, the analytes of interest are detected following chromatographic separation using any one of a number of analytical instruments including, but not limited to, nuclear magnetic resonance imaging (NMR) devices, mass spectrometers (MS), electrochemical arrays (EC), and/or combinations thereof. As used herein, "detecting" or "detected" is defined as determining the presence or amount of an analyte of interest in a test sample. The method of detection is not restricted and may be either qualitative or quantitative.

In another such embodiment of the invention, detecting the analytes of interest comprises analyzing the chromatographically separated analytes using mass spectrometry. As used herein, the terms "mass spectrometry" or "MS" generally refer to methods of filtering, detecting and measuring ions based on their mass-to-charge ratio, or "m/z." In MS techniques, one or more molecules of interest are ionized, and the ions are subsequently introduced into a mass spectrographic instrument (i.e., a mass spectrometer) where, due to a combination of magnetic and electric fields, the ions follow a path in space that is dependent upon their mass ("m") and charge ("z"). See, e.g., U.S. Pat. No. 6,107,623, entitled "Methods and Apparatus for Tandem Mass Spectrometry," which is hereby incorporated by reference in its entirety.

Mass spectrometers which may be utilized in the methods of the invention typically comprise three components: an ionization source, a mass analyzer and a detector. Methods of ionization which may be suitable for use in the methods of the invention include, but are not limited to, chemical ionization, electron ionization, inductively coupled plasma, glow discharge, field desorption, fast atom bombardment, atmospheric pressure chemical ionization, spark ionization and thermal ionization. Types of mass analyzers which may be useful in the methods of the invention may include, but are not limited to, sector, quadrupole, quadrupole ion trap, linear quadrupole ion trap, fourier transform ion cyclotron resonance, orbit trap and time-of-flight. Detectors that may be used in the methods of the invention may include, but are not limited to, electron multipliers or secondary emission multipliers.

In a particular embodiment of the invention, a time-of-flight (ToF) mass analyzer may be used in conjunction with a gas chromatograph, ionization source and detector to detect the ions derived from the analytes of interest. As used herein, a "time-of-flight mass analyzer" is regarded as a specific type of mass analyzer in which ions are introduced from an ionization source and are accelerated by an electric field of known strength. The accelerated ions are introduced into a field-free drift region, where they travel towards a detector which is located at the distal end of the drift region. Ions will separate in the mass analyzer according to their mass-to-charge (m/z) ratios, such that heavier ions will travel more slowly than lighter ions. Such separation results in different arrival times at the detector, where the transit time of each ion is recorded. Data generated by the detection methods described herein are regarded as the "second data set". As used within the context of mass spectrometry analysis, "data" and "data set" means the individual measurements, or the collection of measurements, that are recorded by a detector following the separation of metabolite-derived ions in a mass analyzer.

It is recognized that various methods may be used to enhance the resolution of signals produced by a ToF mass analyzer including, but not limited to, delayed extraction, ion gating or orthogonal acceleration. Additional methods which may be used to enhance the resolution of ToF mass spectrometry include Hadamard transform ToF mass spectrometry, tandem ToF/ToF mass spectrometry, or the use of a reflectron. Various types of recorders may be utilized with a ToF mass spectrometer to record the electrical signals from the detector including, but not limited to, time-to-digital converters or fast analog-to-digital converters.

Methods of the invention also provide means for characterizing the phenotypic profiles or trait profiles of plants or groups of plants. Such phenotypes and traits may be evaluated in plants or groups of plants using any one of a number of assays and techniques which would be known to a person of ordinary skill in the art. Embodiments of the invention include the use of techniques and analyses which detect changes in various plant characteristics including, but not limited to, chemical composition, morphology, biomass or physiological responses to stress conditions. Further, altered physiological properties in plants of the invention may be identified by evaluation of responses to stress conditions, for example, in assays using imposed stress conditions to detect improved responses to water stress, nitrogen deficiency, cold or hot growing conditions, pathogen or insect attack or light deficiency, or alternatively, under naturally present stress conditions, for example, under field conditions. Altered chemical compositions, such as nutritional composition of grain, may be detected by analysis, for example, of composition and content of seed protein, free amino acids, oil, free fatty acids, starch or tocopherols. Biomass measures may be made on greenhouse or field grown plants and may include such measurements as plant height, stem diameter, root and shoot dry weights, partitioning of dry matter among different plant organs and, for corn plants, flowering behavior, ear length, and ear diameter.

Embodiments of the invention further provide methods for collecting phenotypic and trait data on morphological changes by visual observation. Such phenotypic and trait data may include, but is not limited to, characteristics such as normal plants, bushy plants, taller plants, thicker stalks, narrow leaves, striped leaves, knotted phenotype, chlorosis, albino, anthocyanin production, or altered tassels, ears or roots. Other altered phenotypes and traits may be identified by measurements taken under field conditions, such as days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, phenotypic and trait characteristics of harvested grain may be evaluated, including number of kernels per row on the ear, number of rows of kernels on the ear, kernel abortion, kernel weight, kernel size, kernel density and physical grain quality.

In particular embodiments of the invention, visual observation of plant phenotypes and traits may also be collected using an automated system. In one such embodiment, the method of visual observation involves growing plants in a controlled greenhouse environment, transferring plants at selected times to an imaging analysis area where a quantitative, non-destructive light spectrum digital imaging analyzer, preferably having an instrumental variance below about 5%, takes reflected light images of the plant. The analyzer then analyzes those images to determine a value for a phenotypic or trait parameter of interest for the plant. Such an automated system is described in U.S. patent application Ser. No. 11/669,377, which is hereby incorporated by reference in its entirety.

III. Establishing an Unbiased Model

The methods of the invention provide for establishing an unbiased model between at least two groups of plants that can be applied to the metabolic profile of an independent plant to predict a phenotype of interest in the independent plant. The independent plant may be at any stage of development, including an immature plant. Furthermore, the metabolic profile of the independent plant may be characterized at the same age or developmental stage as that of the plants used to establish the unbiased model of the invention or at a different stage as that of the plants used to establish the model.

In one embodiment, pre-processing steps are used to reduce the noise and dimensionality of the chromatography data (first data set) and mass spectroscopy data (second data set) prior to establishing the unbiased models of the invention. The method of the invention encompasses predictive multivariate models combined with highly replicated experiments; thus, pre-processing steps advantageously reduce the noise and dimensionality of the large data sets. As used herein, "pre-processing" of the data sets means to apply statistical analyses to the raw data in order to reduce the noise and dimensionality of the data, as well as reduce potential weighting of the data towards specific metabolites that may produce many mass-to-charge signals. The term "dimensionality" refers to the number of variables under consideration in a data set. The term "noise" refers to the presence of any signal in the data set other than the signals which are desired for analysis. As used within the context of mass spectroscopy analysis, "noise" means low abundant inconsistent chemical-based and electronics-based signal. By "reduce the noise and dimensionality" is meant the use of signal filtering and statistical techniques to reduce the number of variables in the data sets and improve the signal-to-noise ratio of the data.

Such a reduction in dimensionality and noise is advantageous, as the data sets of the invention comprise large numbers of values and each metabolite may produce more than one mass-to-charge fragment value when detected by GC/ToF analysis. In one embodiment of the invention, pre-processing involves assigning the values of the data sets to a common time grid and using a first series of signal filtering and statistical techniques to reduce the noise and dimensionality of the data. Such techniques may include, but are not limited to, smoothing, noise subtraction, thresholding and retention time or retention index alignment. As used herein, "smoothing" describes statistical techniques which create an approximating function that attempts to capture important patterns in the data sets while leaving out noise or other fine-scale structures and/or transient phenomena. "Smoothing" may also refer to chromatogram smoothing. By "thresholding" is intended to assign a minimum value that a signal, detected by mass spectrometry analysis, must achieve in order to be included in the analysis. "Retention time alignment" means to apply a local displacement-based alignment function to the data set using the first chromatogram of the data set as a retention time or retention index alignment reference. Such alignment functions may include, but are not limited to, correlation optimized warping, dynamic time warping and parametic time warping. Subsequent steps for pre-processing the data may also include filtering mass-to-charge fragment×retention time or index combinations using thresholding and consistency functions. Furthermore, mass-to-charge fragment×retention times or index intensities may be normalized to an internal standard mass-to-charge intensity and the sample dry weight. The analysis of data sets using such techniques would be within the ability of a person of ordinary skill in the art.

One or more statistical analyses may be used to pre-process the data in order to reduce the noise and dimensionality. Such analyses may include, but are not limited to, any combination of assigning retention time windows to the data sets derived from mass spectrometry analysis, calculation of a Pearson correlation coefficient for the mass-to-charge fragments within such retention time or retention index windows, clustering of such mass-to-charge fragments and selecting the mass-to-charge fragments with the highest frequency of being a maximum within each one of said clusters to represent the fragments of that cluster in further analysis.

"Retention time windows" refers to specific windows of time during the process of mass spectroscopy analysis during which ion detection data is collected. Such retention time windows may begin with the latest retention time observed in a data set and range in time from about 0.1-1.0 seconds. Retention index windows may also be established within the data sets of the invention. A "Pearson correlation coefficient matrix" is meant to describe a statistical method by which the mass-to-charge fragments within the retention time or retention index windows are correlated to one another. A Pearson correlation is generally used to find a correlation between at least two continuous variables. The value for a Pearson correlation coefficient can fall between −1.0 (i.e., a perfect inverse correlation) and 1.0 (i.e., a perfect correlation), wherein a value of 0.0 indicates no correlation between the variables. A matrix of Pearson correlation coefficients is calculated for all of the ions within the retention time or retention index windows.

As used herein, "clustering" means the use of statistical analyses to assign the data of the invention into subsets (i.e., clusters) so that values in the same cluster are similar in some sense. Such analyses may include, but are not limited to, a K nearest neighbor agglomerative method. As used herein, the "K nearest neighbor" agglomerative method describes statistical analyses wherein a value is classified by a majority vote of its neighbors, with the value being assigned to the class most common amongst its K nearest neighbors, wherein K is typically a small, positive integer. In particular embodiments of the invention, clusters can be made when the calculated neighboring distance in the Pearson correlation coefficient space defined by the retention time or retention index windows is calculated as less than 1.0, and wherein at least five mass-to-charge fragment signals are within the minimum distance. Such mass-to-charge fragment signals which are not within the minimum distance of a five-member cluster may be eliminated from the data set. In further embodiments of the invention, the mass-to-charge fragment signals which have the highest frequency of being the maximum within each of the calculated clusters may be selected to represent that cluster across all samples in the data set.

The invention also provides methods for performing an unbiased, multivariate analysis of the pre-processed data sets to establish an unbiased model, which relates metabolomic data to phenotypic or trait data. As used herein, "unbiased" means that the metabolite data obtained by mass spectrometry analysis is not characterized, identified or otherwise directed to specific metabolites or metabolic processes prior to statistical analysis. It is also recognized that, in certain embodiments, the unbiased model may be an unbiased chemometric model. "Multivariate analysis" is intended to mean the use of any one of a number of statistical analyses, which are known to those of ordinary skill in the art, for analyzing data which arises from more than one variable. Such techniques would allow for the establishment of an unbiased model using the data sets produced by the methods of the invention.

In particular embodiments of the invention, the multivariate analyses used to establish unbiased models may include, but are not limited to, partial least squares analysis (PLS), partial least squares discriminant analysis (PLSDA), principal components analysis (PCA), latent variable techniques, cross-validation techniques, support vector machines or neural networks.

As used herein, "partial least squares analysis" refers to a statistical analysis known to those of ordinary skill in the art which can be used for quantitative predictions of phenotypic outcomes by finding a linear regression model. By "partial least squares discriminant analysis" is meant the use of statistical analyses that discriminates between two or more naturally occurring groups. PLSDA is also known to those of ordinary skill in the art and may be utilized in certain embodiments of the invention where qualitative predictions might be expected. In cases where PLS or PLSDA are used in the invention, a number of latent variables are selected by cross-validation. By "latent variables" it is meant those variables that are not directly observed but are rather inferred (through a mathematical model) from other variables that are observed (directly measured). The number of such latent variables may be determined by "cross-validation", meaning techniques that assess how the results of a statistical analysis will generalize to an independent data set. The process of determining latent variables using cross-validation is within the ability of those of ordinary skill in the art.

Embodiments of the invention also encompass the identification and exclusion of outliers in the data sets. As used herein, "outliers" means the infrequent observations or data points which do not appear to follow the characteristic distribution of the rest of the data. As such, outliers may greatly influence the slope of the regression line and the value of the correlation coefficient. Such outliers may be identified and excluded by statistical methods including, but not limited to, cross-validation and principal component analysis. By "principal component analysis" is meant a statistical analysis that transforms a number of possibly correlated variables into a smaller number of uncorrelated variables called principal components, wherein the first principal component accounts for as much of the variability in the data as possible, and each succeeding component accounts for as much of the remaining variability as possible. The process of identifying outliers using cross-validation or principal component analysis is within the ability of one of ordinary skill in the art.

Further embodiments of the invention provide methods for establishing an unbiased model using support vector machines or neural networks. As used herein, "support vector machines" describe statistical analyses that are linear-classifier algorithms which determine a boundary (i.e., an n-dimensional hyperplane) which distinguishes between class members. The term "neural network" is intended to mean an actual or simulated (e.g., by computer program) network comprised of numerous, independent, highly interconnected artificial neurons which simulate the functions of biological neurons. The process of using support vector machines or neural networks to establish an unbiased model using the data sets of the invention would be within the ability of one of ordinary skill in the art.

Embodiments of the invention also encompass methods for determining the importance of particular metabolites in the unbiased model. Such methods may include, but are not limited to, variable importance for projection (VIP) analyses. As used herein, "VIP analyses" means statistical analyses to determine the value of each variable (i.e., the data points of the metabolic and phenotypic data sets) in fitting the PLS or PLSDA model for both predictors and response. Such VIP analyses may be applied to any of the methods described herein for establishing the unbiased model of the invention.

Methods of the invention also provide for predicting the development of a phenotype of interest or a trait of interest in a plant using an unbiased model. The term "predicting" or "predict" as used herein, or in the more narrow sense the phrase "predicting the development of a phenotype of interest or a trait of interest" means that the future expression of a phenotype in a plant is anticipated. This anticipation is based on the potential for expression of said phenotype of interest or trait of interest that the plant exhibits at the point in time when the methods of the present invention are applied. As such, said point in time is temporally earlier than the point in time corresponding to the future expression of the phenotype of interest or trait of interest which is being predicted. The term "predisposed", as used herein, is meant to describe a plant which is genetically or environmentally predetermined to develop a phenotype of interest or a trait of interest.

The method of predicting a phenotype of interest or a trait of interest in a plant may vary depending upon the embodiment of the invention used to establish the unbiased model. For example, in one embodiment, the unbiased model may allow for a quantitative prediction, wherein partial least squares analysis may be used to establish a linear correlation between the metabolic profiles and the phenotypic or trait profiles within a training set. Subsequently, the unbiased model can then be applied to the metabolic profile of an independent plant in order to quantitatively predict the development of a phenotype or trait.

In another such embodiment, the unbiased model may allow for a qualitative prediction, wherein PLSDA may be used to establish a correlation between the metabolic profiles and the phenotypic or trait profiles within a training set. In PLSDA, each plant or group of plants is assigned to a class, i.e., plants that exhibit a phenotype or trait and plants that do not. Subsequently, the PLSDA model can then be applied to the metabolic profile of an independent plant in order to predict which class the plant will most closely resemble. In a further embodiment, the probability of a plant developing a phenotype or trait may be calculated using the PLSDA model, as described in the Examples presented herein below.

IV. Plants and Conditions

The invention provides methods for the characterization of metabolic profiles, phenotypic profiles and trait profiles in two or more groups of plants in order to establish an unbiased model. The methods of the invention further encompass immature, independent plants whose phenotypes or traits are predicted based on the application of the unbiased model to their metabolome.

As described herein, the term "groups of plants" means any set of plants which share at least one common feature. Such a common feature may include, but is not limited to, high genetic similarity (e.g., a taxonomic unit, inbred line or hybrid species), a specific mechanism of nitrogen fixation or metamorphosis, the presence of distinct anatomical structures, or the production of a specific type of commercially important matter. A person of ordinary skill in the art could readily identify "groups of plants" which would be appropriate for the methods taught by the invention. In one embodiment of the invention, the two or more groups of plants which are used to establish the unbiased model are of the same genotype and grown under precision growth conditions. As used herein, "precision growth conditions" refers to growth in a greenhouse under controlled light, temperature, water, nutrients and the like.

As used herein, the term "independent plant" means a plant which was not a member of any one of the groups of plants that were used to establish the unbiased model. In one embodiment of the invention, the unbiased model of the invention is applied to the metabolome of the independent plant to predict the expression of a phenotype of interest in the independent plant. In such an embodiment, an independent plant may not be fully mature when its metabolome is characterized. A plant which is not "mature" or is "immature" may include, but is not limited to, plants which are not fully grown or are not ready for harvest. Such independent plants may be grown under precision growth conditions or in a natural environment, and may be grown at the same or different location than those groups of plants which were used to establish the unbiased model of the invention. Additionally, such independent plants may be grown at the same time or at a different time than those plants which were used to establish the unbiased model of the invention. Furthermore, such independent plants may have the same genetic background or a different genetic background than those plants which were used to establish the unbiased model of the invention.

The two or more groups of plants used to establish the unbiased model should preferably exhibit different phenotypes or different traits, be grown under different environmental conditions, or both. Such different phenotypes or traits may be the result of traditional plant breeding techniques, such as hybridization, cross-breeding, back-crossing and other techniques known to those of ordinary skill in the art. Additionally, different phenotypes may be the result of a transgenic event in some or all of the groups of plants which are used to establish the unbiased model. Transgenes of interest which may be utilized in the invention are further described herein below. Phenotypes of interest and traits of interest which may be evaluated by the methods of the present invention may include, but are not limited to, plant growth, total plant area, biomass, dry shoot weight, yield, yield drag, nitrogen utilization efficiency, water use efficiency, pest resistance, disease resistance, transgene effects, response to chemical treatment, stress tolerance, gas exchange parameters, days to silk, days to shed, germination rate, relative maturity, lodging, ear height, flowering time, stress emergence rate, leaf senescence rate, canopy photosynthesis rate, silk emergence rate, anthesis to silking interval, percent recurrent parent, leaf angle, canopy width, leaf width ear fill, scattergrain, root mass, stalk strength, seed moisture, greensnap, shattering, visual pigment accumulation, kernels per ear, ears per plant, kernel size, kernel density, leaf nitrogen content and grain nitrogen content.

In further embodiments of the invention, the two or more groups of plants which are used to establish the unbiased model may also be grown under different environmental conditions from one another. Such conditions may include natural or man-made conditions including, but not limited to, temperature, soil moisture, nitrogen level, insect pressure, disease pressure, soil type, pesticide treatment, herbicide treatment, day length, planting density, light intensity, light quality, tillage practice, day of planting, carbon dioxide levels, oxygen levels, nutrient deficiency, as well as the presence of heavy metals, pathogens (e.g., bacteria, fungi, nematodes, viruses etc.), organisms (e.g., insects) and other conditions commonly known to those of skill in the art that affect plant growth and/or yield.

Any gene can be evaluated in the methods of the invention. Such evaluation includes the expression of the gene in a plant of interest as well as reducing the expression of the gene in a plant. Genes of interest which may be evaluated in the methods of the invention are reflective of the commercial markets and interests of those involved in the development of the crop. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Ill.), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

Genes encoding disease resistance traits include detoxification genes, such as against fumonosin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene); glyphosate (e.g., the EPSPS gene and the GAT gene; see, for example, U.S. Publication No. 20040082770 and WO 03/092360); or other such genes known in the art. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

The quality of grain is reflected in traits such as levels and types of oils, saturated and unsaturated, quality and quantity of essential amino acids, and levels of cellulose. In corn, modified hordothionin proteins are described in U.S. Pat. Nos. 5,703,049, 5,885,801, 5,885,802, and 5,990,389.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

In one embodiment, groups of any plant species may be used to establish the unbiased models of the invention or be the independent plant(s) whose phenotype(s) or trait(s) is (are) predicted using the unbiased models of the invention. As used herein, the term "plant" also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

Plants which may be utilized in the methods of the invention include, but are not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables of interest include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers of interest that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Hardwood trees can also be employed including ash, aspen, beech, basswood, birch, black cherry, black walnut, buckeye, American chestnut, cottonwood, dogwood, elm, hackberry, hickory, holly, locust, magnolia, maple, oak, poplar, red alder, redbud, royal paulownia, sassafras, sweetgum, sycamore, tupelo, willow, yellow-poplar.

In specific embodiments, plants of the present invention are crop plants (for example, corn, alfalfa, sunflower, *Brassica*, soybean, cotton, safflower, peanut, *sorghum*, wheat, millet, tobacco, etc.). In other embodiments, corn and soybean and sugarcane plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Other plants of interest including Turfgrasses such as, for example, turfgrasses from the genus *Poa, Agrostis, Festuca, Lolium*, and *Zoysia*. Additional turfgrasses can come from the subfamily Panicoideae. Turfgrasses can further include, but are not limited to, Blue gramma (*Bouteloua gracilis* (H.B.K.) Lag. Ex Griffiths); Buffalograss (*Buchloe dactyloids* (Nutt.) Engelm.); Slender creeping red fescue (*Festuca rubra* ssp. *Litoralis*); Red fescue (*Festuca rubra*); Colonial bentgrass (*Agrostis tenuis* Sibth.); Creeping bentgrass (*Agrostis palustris* Huds.); Fairway wheatgrass (*Agropyron cristatum* (L.) Gaertn.); Hard fescue (*Festuca longifolia* Thuill.); Kentucky bluegrass (*Poa pratensis* L.); Perennial ryegrass (*Lolium perenne* L.); Rough bluegrass (*Poa trivialis* L.); Sideoats grama (*Bouteloua curtipendula* Michx. Torr.); Smooth bromegrass (*Bromus inermis* Leyss.); Tall fescue (*Festuca arundinacea* Schreb.); Annual bluegrass (*Poa annua* L.); Annual ryegrass (*Lolium multiflorum* Lam.); Redtop (*Agrostis alba* L.); Japanese lawn grass (*Zoysia japonica*); bermudagrass (*Cynodon dactylon; Cynodon* spp. L. C. Rich; *Cynodon transvaalensis*); Seashore paspalum (*Paspalum vaginatum* Swartz); Zoysiagrass (*Zoysia* spp. Willd; *Zoysia japonica* and *Z. matrella* var. *matrella*); Bahiagrass (*Paspalum notatum* Flugge); Carpetgrass (*Axonopus affinis* Chase); Centipedegrass (*Eremochloa ophiuroides* Munro Hack.); Kikuyugrass (*Pennisetum clandesinum* Hochst Ex Chiov); Browntop bent (*Agrostis tenuis* also known as *A. capillaris*); Velvet bent (*Agrostis canina*); Perennial ryegrass (*Lolium perenne*); and, St. Augustinegrass (*Stenotaphrum secundatum* Walt. Kuntze). Additional grasses of interest include switchgrass (*Panicum virgatum*).

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXAMPLES

Example 1

Quantitative Prediction of Relative Plant Biomass and Nitrogen Use Efficiency Under Nitrogen Deprivation Relative plant biomass and nitrogen use efficiency (NUE) were predicted in corn using the methods of the invention. Plant biomass was observed as an indicator of plant productivity under different treatment conditions. As used herein, "nitrogen use efficiency" or "NUE" is defined as the ratio of aerial plant biomass under low nitrogen conditions to the aerial plant biomass under normal nitrogen conditions. Relative plant biomass and NUE were predicted using 250 inbred corn lines. Twelve replicates of each inbred line were grown under normal nitrogen solutions (6.5 mMol nitrate) or low nitrogen solutions (1.0 mMol nitrate). Six batches of each group of plants were grown over six time periods from August to January, and the plants were sampled for metabolomics at vegetative stage 7. Characterization of plant metabolic and phenotypic profiles was accomplished as described herein below.

Gas Chromatograph and Time of Flight Mass Spectrometer Settings and Methods:

To characterize the metabolic profile of each plant or group of plants, metabolites were extracted from three lyophilized leaf discs of approximately 3 mg combined dry weight. Five hundred microliters of chloroform:methanol: water (2:5:2, v/v/v) containing 0.015 mg ribitol internal standard were added to each sample in a 1.1 mL polypropylene microtube containing two 5/32" stainless steel ball bearings. Samples were homogenized in a 2000 Geno/Grinder ball mill at setting 1,650 for 1 minute and then rotated at 4° C. for 30 minutes. Samples were then centrifuged at 1,454 g for 15 minutes at 4° C. Next, 300 µL aliquots were transferred to 1.8 mL high recovery GC vials and subsequently evaporated to dryness in a speed vac. The dried residues were re-dissolved in 50 µL of 20 mg mL$^{-1}$ methoxyamine hydrochloride in pyridine, capped, and agitated with a vortex mixer. The samples were incubated in an orbital shaker at 30° C. for 90 minutes to form methoxyamine derivatives. Eighty microliters of N-methyl-N-(trimethylsilyl) trifluoroacetamide (MSTFA) were added to each sample to form trimethylsilyl derivatives. The MSTFA delivery to individual samples was performed by the gas chromatograph autosampler 30 minutes prior to injection, greatly minimizing sample variability due to differences in the state of derivatization.

Trimethylsilyl derivatives were separated by gas chromatography on a Restek 30 m×0.25 mm id×0.25 μm film thickness Rtx®-5Sil MS column with 10 m integra guard column. One microliter injections were made with a 1:10 split ratio using a CTC Combi PAL autosampler. The Agilent 6890N gas chromatograph was programmed for an initial temperature of 80° C. for 5 minutes, increased to 350° C. at 18° minute$^{-1}$ where it was held for 2 minutes before being cooled rapidly to 80° C. in preparation for the next run. The injector and transfer line temperatures were 230° C. and 250° C., respectively, and the source temperature was 200° C. Helium was used as the carrier gas with a constant flow rate of 1 mL minute$^{-1}$ maintained by electronic pressure control. Data acquisition was performed on a LECO Pegasus III time-of-flight mass spectrometer with an acquisition rate of 10 spectra second$^{-1}$ in the mass range of m/z 45-600. An electron beam of 70 eV was used to generate spectra. Detector voltage was approximately 1550-1800 V depending on the detector age. An instrument auto tune for mass calibration using perfluorotributylamine (PFTBA) was performed prior to each GC sequence.

Pre-Processing of Raw GC/ToFMS Data:

Genedata's Expressionist Refiner MS was used to assemble and align the GC/ToFMS data with feature selection and noise reduction. The first step was to generate and fit all of the data to a common time grid. Noise reduction was then performed using smoothing and thresholding. The retention times were then aligned using a local displacement function. The first chromatogram was used as a retention time alignment reference. The output of this workflow was a table of intensities associated with retention times or retention indices and mass-to-charge ratios representing a molecular fragment from the electron impact detected on the mass spectrometer.

The data was then loaded into the Matlab workspace for further processing. Starting with the latest retention time, the correlation between all of the m/z data points within a retention time window of 0.5 seconds was determined. Within this retention time window, a Pearson correlation coefficient matrix was calculated across all samples. The m/z channels were assembled into clusters using the K nearest neighbor agglomerative method. Clusters were made when the calculated neighboring distance was less than 1. A cluster further required more than five mass-to-charge fragment channels to be included in the modeling data. If a mass-to-charge fragment signal channel was not within the minimum distance of a five member cluster it was eliminated from the table of data. This process was repeated until all data channels were clustered or eliminated on a single basis. Once all of the correlated clusters within a retention time window had been calculated, the mass-to-charge fragment channel with the highest frequency of being the maximum within each sample cluster was selected as the intensity for this cluster across all samples.

Modeling:

In modeling, all of the data was pre-processed by autoscaling, or dividing each data channel by its standard deviation in the data set followed by mean centering. In each case, partial least squares (PLS) multivariate calibrations were built to predict a quantitative outcome from the metabolome. In the cases where qualitative predictions were expected, these states were digitally represented as ones and zeros. This practice is commonly referred to partial least squares discriminant analysis (PLSDA). In each case cross-validation or validation were used to select the number of latent variables. In no case did the number of latent variables exceed five and in most it was only two. Outliers were identified using principal component analysis and cross validation. All modeling was performed using the PLSToolbox from Eigenvector Research.

Quantitative Prediction of Relative Plant Biomass Under Nitrogen Deprivation:

As previously described, nitrogen use efficiency was tested in 250 inbred corn lines grown in pots in a greenhouse. Twelve replicates of each inbred line were fed either normal nitrogen solutions (6.5 mMol nitrate) or low nitrogen solutions (1.0 mMol nitrate). Six batches of each group of plants were grown over six time periods from August to January, and the plants were sampled for metabolomics at vegetative stage 7. to monitor plant productivity, the aerial biomass of each plant was cut weighed and dried to be weighed again. Plant phenotypes were also monitored using the Lemnatech imaging system. These images were used to calculate the specific growth rate, the total leaf area, and the basic RGB color image analysis.

In this example, plant productivity was assessed by measuring changes in the dry shoot weight of plants in response to low or normal nitrogen. Because it was not possible to give the same plant normal nitrogen and low nitrogen to determine the productive response, averages for the inbred lines treated with low and normal nitrogen were used in the calculations.

Prediction of biomass within each treatment group was first calculated using PLS leave-one-out cross-validation of the phenotypic and metabolomic data for each treated inbred line. The prediction for each inbred was made with the inbred removed from the calibration per the leave-one-out analysis. These predictions are shown in FIGS. 1 and 2. FIG. 1 shows actual dry shoot weight versus the predicted dry shoot weight of the inbred lines grown under normal nitrogen conditions, wherein the $R^2$ value=0.6723 and the Root-Mean-Square Error of Cross-Validation (RMSECV)=0.6573. FIG. 2 shows actual dry shoot weight versus the predicted dry shoot weight of the inbred lines grown under low nitrogen conditions, wherein the $R^2$ value=0.4235 and the RMSECV=0.4607.

Prediction of dry shoot weight in the low nitrogen-treated inbred lines was then predicted using PLS cross-validation and the average metabolome of the plants given normal nitrogen levels. FIG. 3 shows actual dry shoot weight of the low nitrogen inbred lines versus the predicted dry shoot weight of the inbred lines, wherein the $R^2$ value=0.2867 and the RMSECV=0.5136.

Prediction of NUE for each of the inbred lines was then calculated. As stated, NUE was determined to be the ratio of aerial biomass of low nitrogen-treated inbred lines to the aerial biomass of normal nitrogen-treated inbred lines. In this example, the NUE was predicted for each inbred line using PLS cross-validation and the metabolic phenotype data from the normal nitrogen-treated inbred lines. This prediction was then compared to the observed values shown in FIG. 4, wherein the metabolomics-based PLS model predicted genotype specific relative dry shoot weight of between plants deprived of nitrogen and those receiving sufficient nitrogen is plotted against the relative dry shoot weight.

Example 2

Qualitative Class Prediction for Ranking Transgenes in Response to Drought

A PLSDA classification model was used to predict the qualitative effect of two drought-tolerance genes in transgenic corn plants. As demonstrated herein below, the metabolome can be used to gauge the efficacy of genetic modifications by comparing the proximity of the stressed metabolome to a PLSDA classification model built between unmodified restricted water plants and unmodified well-watered plants. This can be accomplished through a dimensionally-reduced class prediction. In the PLSDA classification model, each metabolite is weighted according to its ability to separate the treatments. The model can then be used to predict the transgenically modified plants' response to stress.

In the present example, two drought-tolerance constructs were tested in a greenhouse drought assay. Control plants were used that had independent planting dates for each of the constructs. Transgenic plant seeds were obtained from the first segregating ear of seed generated from transformation. Fifteen of the null segregants and fifteen of the positive segregants were each grown with sufficient water (well-watered) or restricted water. A PLSDA model was built using the top 20 predictive weight ranking metabolites in the null segregants as determined by a variable importance projection calculation. This model captures the metabolic changes produced by drought stress across a range of genotypes and environments, which are illustrated in FIG. 5.

The model, which was derived using phenotypic and metabolic data from the null segregants, was then applied to the metabolic data of the transgene positive segregants to predict whether the plants would exhibit a restricted water phenotype or a well-watered phenotype. For some transgene positive segregants, their predicted class was statistically separated from the null segregants in the direction of the well-watered metabolome. As illustrated by FIG. 6, the left half of the figure shows the predictions for the null segregants used to make the model. The right half of the figure contains the predictions of the positive segregants. The mean numerical-represented class prediction for each of the seven events ranked with the PLSDA model are given in Table I. The transgenic events whose metabolic profiles were significantly altered in the direction of the well-water null segregants are highlighted in grey. The events highlighted in grey also had significantly different phenotypes including, but not limited to, increased plant biomass.

TABLE I

The numerical-represented class predictions statistically different for the drought assay are given for seven events from FIG. 6.

| Event | Null mean | Event mean | Null-Event | Std. Dev. Null | Std. Dev. Event | Pvalue |
|---|---|---|---|---|---|---|
| 1 | 0.1366 | 0.0191 | 0.1175 | 0.2379 | 0.2393 | 5.49E−02 |
| 2 | 0.1366 | 0.3857 | −0.2492 | 0.2379 | 0.2090 | 1.07E−04 |
| 3 | 0.1366 | 0.2049 | −0.0683 | 0.2379 | 0.3022 | 1.61E−01 |
| 4 | 0.1366 | 0.0858 | 0.0508 | 0.2379 | 0.2218 | 2.27E−01 |
| 5 | 0.1366 | 0.2671 | −0.1305 | 0.2379 | 0.2867 | 3.64E−02 |
| 6 | 0.1366 | 0.2830 | −0.1465 | 0.2379 | 0.3557 | 2.08E−02 |
| 7 | 0.1366 | 0.5034 | −0.3668 | 0.2379 | 0.1977 | 2.93E−07 |

Example 3

Qualitative Prediction of Transgene Responses

In the widescale testing of transgenic hybrids expressing a gene of interest, a high yielding preferred phenotype was observed. Twenty two hybrids expressing the gene of interest were planted in Chile in a field experiment. Hybrids from the same genotype with different gene stacks were also included to provide metabolic contrasts. Based on the extensive product testing, hybrids were classified according to the observation of the yield effects.

A PLSDA model was calculated using a single genotype with the gene of interest incorporated into the hybrid from each of the parents. In the Chile experiment, one of these common parent hybrids exhibited a high yielding phenotype, while the other did not. The classes in this PLSDA model were designated high yield and other. The model was improved through variable selection, using a genetic algorithm and the other hybrids as a validation set. Using the predictions from the replicates, a probability of high yielding phenotype was estimated from the distribution of predictions compared to the calibration hybrid predictions. Table II contains the metabolome-estimated probability of observing the desired high yield phenotype. Hybrids that are high yielding are indicated with a plus sign.

TABLE II

A phenotype classifying PLSDA model with metabolome input was constructed from a single genotypic background and was able to predict the observed high yield phenotype in other genotypes. Positive phenotypes observed in large scale testing are indicated with plus signs.

| Hybrid | Probability of High Yield | Observed high yield |
|---|---|---|
| 1 | 0.997 | |
| 2 | 0.972 | + |
| 3 | 0.938 | + |
| 4 | 0.935 | + |
| 5 | 0.767 | + |
| 6 | 0.737 | + |
| 7 | 0.578 | |
| 8 | 0.538 | |
| 9 | 0.488 | + |
| 10 | 0.411 | + |
| 11 | 0.34 | |
| 12 | 0.209 | |
| 13 | 0.197 | |
| 14 | 0.184 | |
| 15 | 0.128 | |
| 16 | 0.115 | |
| 17 | 0.053 | |
| 18 | 0.05 | |
| 19 | 0.039 | |
| 20 | 0.029 | |
| 21 | 0.026 | |
| 22 | 0.024 | |

That which is claimed:

1. An unbiased method for selecting and growing at least one independent plant having a predicted phenotype, said method comprising:
   a) establishing phenotypic profiles of at least two groups of plants, wherein said at least two groups of plants have different phenotypes, or wherein said at least two groups of plants are grown under different environmental conditions;
   b) establishing for each group of plants of said at least two groups of plants a metabolic profile comprising an entire set of metabolites, said establishing comprising i) extracting metabolites from each group of plants; ii) separating said metabolites by chromatography to generate a first set of data; iii) detecting the mass-to-charge fragments produced by said metabolites using mass spectrometry to generate a second set of data; iv) pre-processing said first set of data and said second set of data to align, reduce noise and dimensionality, and normalize, wherein the entire set of metabolites for each group of plants comprises all of the metabolites that are detected and pre-processed to eliminate bias;

c) building a model using the pre-processed data of step b) to predict a quantitative or qualitative phenotype;

d) selecting variables by validation or cross-validation of step c);

e) establishing a metabolic profile of the at least one independent plant, f) applying the model of c) to the metabolic profile of the independent plant to predict expression of the quantitative or qualitative phenotype of the at least one independent plant; and g) growing the selected at least one independent plant predicted to express the qualitative or quantitative phenotype, wherein the selected plant has the same genetic background or a different genetic background as at least one of the groups of plants used to establish the model.

2. The method of claim 1, wherein said at least one independent plant comprises at least one transgene.

3. The method of claim 1, wherein said method of building a model comprises the use of partial least squares discriminant analysis.

4. The method of claim 1, wherein outliers in said model are identified by principal component analysis and cross-validation.

5. The method of claim 1, wherein variable importance projection analyses are used to estimate importance of said metabolites in said unbiased method.

6. The method of claim 1, wherein separation of said metabolites by chromatography is performed using gas chromatography.

7. The method of claim 1, wherein said metabolites are detected by mass spectrometry using a time-of-flight mass spectrometer.

8. The method of claim 7, wherein said pre-processing of said first set of data and said second set of data to reduce the noise and dimensionality comprises: a) fitting the mass-to-charge fragments to a common time grid; b) reducing noise and dimensionality using statistical analyses, wherein said statistical analyses includes smoothing, noise subtraction or thresholding; c) aligning mass-to-charge fragment retention times or retention indices using a local displacement function; d) filtering mass-to-charge fragment×retention times or index combinations using thresholding and consistency functions; and, e) normalizing said mass-to-charge fragment×retention times or index intensities for internal standard mass-to-charge intensity and sample dry weight.

9. The method of claim 8, further comprising the steps of: a) establishing specific retention time or retention index windows; b) determining a correlation between said mass-to-charge fragments identified within said specific retention time or retention index windows; c) calculating a Pearson correlation coefficient matrix for said mass-to-charge fragments; d) clustering said mass-to-charge fragments using a K nearest neighbor agglomerative method, wherein clusters are made when a calculated neighboring distance is less than 1, and wherein said clusters require more than 5 mass-to-charge fragments; e) eliminating mass-to-charge fragments that are not within said calculated neighboring distance of said clusters; and, f) selecting said mass-to-charge fragments that exhibit a highest frequency of being a maximum within each one of said clusters to represent each said cluster in said unbiased method.

10. The method of claim 1, wherein said at least two groups of plants are grown under precision growth conditions.

11. The method of claim 1, wherein said at least one independent plant is grown under precision growth conditions or under natural conditions.

12. The method of claim 1, wherein said at least two groups of plants possess the same genetic background.

13. The method of claim 12, wherein said at least one independent plant possesses the same genetic background as said at least two groups of plants.

14. The method of claim 12, wherein said at least one independent plant possesses a different genetic background from said at least two groups of plants.

15. The method of claim 1, wherein said at least one independent plant is grown under the same environmental conditions as said at least two groups of plants.

16. The method of claim 1, wherein said at least one independent plant is grown under different environmental conditions as said at least two groups of plants.

17. The method of claim 1, wherein said at least one independent plant is grown at the same time as said at least two groups of plants.

18. The method of claim 1, wherein said at least one independent plant is grown at a different time than said at least two groups of plants.

19. The method of claim 1, wherein said at least one independent plant is grown at the same location as said at least two groups of plants.

20. The method of claim 1, wherein said at least one independent plant is grown at a different location than said at least two groups of plants.

21. The method of claim 1, wherein said different phenotypes of said at least two groups of plants are selected from the group consisting of plant growth, total plant area, biomass, dry shoot weight, yield, yield drag, nitrogen utilization efficiency, water use efficiency, pest resistance, disease resistance, transgene effects, response to chemical treatment, stress tolerance, gas exchange parameters, days to silk, days to shed, germination rate, relative maturity, lodging, ear height, flowering time, stress emergence rate, leaf senescence rate, canopy photosynthesis rate, silk emergence rate, anthesis to silking interval and percent recurrent parent.

22. The method of claim 1, wherein said different environmental conditions under which said at least two groups of plants are grown are selected from the group consisting of temperature, soil moisture, nitrogen level, insect pressure, disease pressure, soil type, pesticide treatment, herbicide treatment, day length, planting density, light intensity, light quality, tillage practice, day of planting, carbon dioxide levels and oxygen levels.

23. The method of claim 1, wherein said at least two groups of plants, or said at least one independent plant, are monocots or dicots.

24. The method of claim 23, wherein said monocots or dicots are maize, rice, barley, oats, millet, wheat, grasses, soybean, cotton, sunflower, safflower, *Arabidopsis*, tobacco, rapeseed, sugarcane, alfalfa, canola, clover, tomato, potato, cassava or *sorghum*.

25. The method of claim 1, further comprising, obtaining seeds from the selected at least one independent plant predicted to express the qualitative or quantitative phenotype, wherein the selected plant has the same genetic background or a different genetic background than at least one of the groups of plants used to establish the model.

26. The method of claim 1, further comprising, growing to maturity the selected at least one independent plant predicted to express the qualitative or quantitative phenotype.

27. An unbiased method for selecting and growing at least one independent plant having a predicted trait, said method comprising:
- a) establishing trait profiles of said at least two groups of plants, wherein said at least two groups of plants have different traits, or wherein said at least two groups of plants are grown under different environmental conditions;
- b) establishing for each group of plants of said at least two groups of plants a metabolic profile comprising an entire set of metabolites, said establishing comprising i) extracting metabolites from each group of plants; ii) separating said metabolites by chromatography to generate a first set of data; iii) detecting the mass-to-charge fragments produced by said metabolites using mass spectrometry to generate a second set of data; iv) pre-processing said first set of data and said second set of data to align, reduce noise and dimensionality and normalize, wherein the entire set of metabolites for each group of plants comprises all of the metabolites that are detected and pre-processed to eliminate bias;
- c) building a model using the pre-processed data of step b) to predict a quantitative or qualitative trait;
- d) selecting variables by validation or cross-validation of step c);
- e) establishing a metabolic profile of at least one independent plant,
- f) applying the model of c) to the metabolic profile of the independent plant to predict expression of said qualitative or quantitative trait in said at least one independent plant; and
- g) growing the selected at least one independent plant predicted to express the qualitative or quantitative phenotype, wherein the selected plant has the same genetic background or a different genetic background as at least one of the groups of plants used to establish the model.

28. The method of claim 27, wherein said at least one independent plant is not mature.

29. The method of claim 27 wherein said at least one independent plant comprises at least one transgene.

30. The method of claim 27, wherein said model comprises the use of partial least squares discriminant analysis.

31. The method of claim 27, wherein outliers in said model are identified by principal component analysis and cross-validation.

32. The method of claim 27, wherein variable importance projection analyses are used to estimate importance of said metabolites in said model.

33. The method of claim 27, wherein separation of said metabolites by chromatography is performed using gas chromatography.

34. The method of claim 27, wherein said metabolites are detected by mass spectrometry using a time-of-flight mass spectrometer.

35. The method of claim 34, wherein said pre-processing of said first set of data and said second set of data to reduce the noise and dimensionality comprises: a) fitting the mass-to-charge fragments to a common time grid; b) reducing noise and dimensionality using statistical analyses, wherein said statistical analyses includes smoothing, noise subtraction or thresholding; c) aligning retention times or retention indices using a correlation-based alignment function; d) filtering mass-to-charge fragment×retention times or index combinations using thresholding and consistency functions; and e) normalizing said mass-to-charge fragment×retention times or index intensities for internal standard mass-to-charge intensity and sample dry weight.

36. The method of claim 35, further comprising the steps of: a) establishing specific retention time or retention index windows; b) determining a correlation between said mass-to-charge fragments identified within said specific retention time windows; c) calculating a Pearson correlation coefficient matrix for said mass-to-charge fragments; d) clustering said mass-to-charge fragments using a K nearest neighbor agglomerative method, wherein clusters are made when a calculated neighboring distance is less than 1, and wherein said clusters require more than 5 mass-to-charge fragments; e) eliminating mass-to-charge fragments that are not within said calculated neighboring distance of said clusters; and, f) selecting said mass-to-charge fragments that exhibit a highest frequency of being a maximum within each one of said clusters to represent each said cluster in said unbiased method.

37. The method of claim 27, wherein said at least two groups of plants are grown under precision growth conditions.

38. The method of claim 27, wherein said at least one independent plant is grown under precision growth conditions or under natural conditions.

39. The method of claim 27, wherein said at least two groups of plants possess the same genetic background.

40. The method of claim 39, wherein said at least one independent plant possesses the same genetic background as said at least two groups of plants.

41. The method of claim 39, wherein said at least one independent plant possesses a different genetic background from said at least two groups of plants.

42. The method of claim 27, wherein said at least one independent plant is grown under the same environmental conditions as said at least two groups of plants.

43. The method of claim 27, wherein said at least one independent plant is grown under different environmental conditions as said at least two groups of plants.

44. The method of claim 27, wherein said at least one independent plant is grown at the same time as said at least two groups of plants.

45. The method of claim 27, wherein said at least one independent plant is grown at a different time than said at least two groups of plants.

46. The method of claim 27, wherein said at least one independent plant is grown at the same location as said at least two groups of plants.

47. The method of claim 27, wherein said at least one independent plant is grown at a different location than said at least two groups of plants.

48. The method of claim 27, wherein said different traits of said at least two groups of plants are selected from the group consisting of leaf angle, canopy width, leaf width ear fill, scattergrain, root mass, stalk strength, seed moisture, greensnap, shattering, visual pigment accumulation, kernels per ear, ears per plant, kernel size, kernel density, leaf nitrogen content and grain nitrogen content.

49. The method of claim 27, wherein said different environmental conditions under which said at least two groups of plants are grown are selected from the group consisting of temperature, soil moisture, nitrogen level, insect pressure, disease pressure, soil type, pesticide treatment, herbicide treatment, day length, planting density, light intensity, light quality, tillage practice, day of planting, carbon dioxide levels and oxygen levels.

50. The method of claim 27, wherein said at least two groups of plants, or said at least one independent plant, are monocots or dicots.

51. The method of claim 50, wherein said monocots or dicots are maize, rice, barley, oats, millet, wheat, grasses, soybean, cotton, sunflower, safflower, *Arabidopsis*, tobacco, rapeseed, sugarcane, alfalfa, canola, clover, tomato, potato, cassava or *sorghum*.

52. The method of claim 27, further comprising, obtaining seeds from the selected at least one independent plant predicted to express the qualitative or quantitative phenotype, wherein the selected plant has the same genetic background or a different genetic background than at least one of the groups of plants used to establish the model.

53. The method of claim 27, further comprising, growing to maturity the selected at least one independent plant predicted to express the qualitative or quantitative phenotype.

54. An unbiased method for selecting and growing at least one independent transgenic plant having a predicted phenotype, said method comprising:
   a) establishing phenotypic profiles of said at least two groups of plants, wherein said at least two groups of plants have different phenotypes, or wherein said at least two groups of plants are grown under different environmental conditions;
   b) establishing for each group of plants a metabolic profile comprising an entire set of metabolites, said establishing comprising i) characterizing the metabolic profiles of said at least two groups of plants using chromatography and mass spectrometry to produce sets of data; ii) pre-processing said data to align the data, reduce noise and dimensionality of the data and normalize the data, clustering, and selecting mass-to-charge fragments for use in said unbiased method; iii) building, with the pre-processed data of ii), a model to predict a quantitative or qualitative phenotype; iv) selecting variables by validation or cross-validation of step iii), wherein the entire set of metabolites for each group of plants comprises all of the metabolites that are detected and pre-processed to eliminate bias;
   c) establishing the metabolic profile of at least one transgenic independent plant, wherein said at least one transgenic independent plant is not mature;
   d) applying the model of b) iii) to the metabolic profile of the independent transgenic plant to predict expression of said quantitative or qualitative phenotype in said at least one transgenic independent plant; and
   e) growing the selected at least one independent transgenic plant predicted to express the qualitative or quantitative phenotype, wherein the selected plant has the same genetic background or a different genetic background as at least one of the groups of plants used to establish the model.

55. The method of claim 54, further comprising, obtaining seeds from the selected at least one independent plant predicted to express the qualitative or quantitative phenotype, wherein the selected plant has the same genetic background or a different genetic background than at least one of the groups of plants used to establish the model.

56. The method of claim 54, further comprising, growing to maturity the selected at least one independent plant predicted to express the qualitative or quantitative phenotype.

57. An unbiased method for selecting and growing at least one independent transgenic plant having a predicted trait, said method comprising:
   a) establishing trait profiles of at least two groups of plants, wherein said at least two groups of plants have different traits, or wherein said at least two groups of plants are grown under different environmental conditions;
   b) establishing for each group of plants a metabolic profile comprising an entire set of metabolites, said establishing comprising i) characterizing the metabolic profiles of said at least two groups of plants using chromatography and mass spectrometry to produce sets of data; ii) pre-processing said data to align the data, reduce noise and dimensionality of the data and normalize the data, clustering, and a K nearest neighbor agglomerative method to select mass-to-charge fragments for use in said unbiased method; iii) building, with the pre-processed data of ii), a model to predict quantitative or qualitative traits; iv) selecting variables by validation or cross-validation of step iii), wherein the entire set of metabolites comprises all of the metabolites that are detected and pre-processed to eliminate bias;
   c) establishing the metabolic profile of at least one independent transgenic plant, wherein said at least one independent transgenic plant is not mature;
   d) applying the model of b) iii) to the metabolic profile of the independent transgenic plant to predict expression of said quantitative or qualitative trait in said at least one independent transgenic plant;
   e) growing the selected at least one independent transgenic plant predicted to express the qualitative or quantitative trait, wherein the selected plant has the same genetic background or a different genetic background as at least one of the groups of plants used to establish the model.

58. The method of claim 57, further comprising, obtaining seeds from the selected at least one independent plant predicted to express the qualitative or quantitative phenotype, wherein the selected plant has the same genetic background or a different genetic background than at least one of the groups of plants used to establish the model.

59. The method of claim 57, further comprising, growing to maturity the selected at least one independent plant predicted to express the qualitative or quantitative phenotype.

* * * * *